United States Patent
Miki et al.

(10) Patent No.: US 9,138,734 B2
(45) Date of Patent: Sep. 22, 2015

(54) VISIBLE LIGHT-RESPONSIVE PHOTOCATALYST COATING MATERIAL, COATED ARTICLE, ALLERGEN INACTIVATION METHOD

(75) Inventors: Shinichiro Miki, Osaka (JP); Koichi Takahama, Hyogo (JP); Kensaku Kinugawa, Nara (JP); Kazuhito Hashimoto, Tokyo (JP); Kayano Sunada, Tokyo (JP)

(73) Assignees: PANASONIC CORPORATION, Osaka (JP); THE UNIVERSITY OF TOKYO, Tokyo (JP)

( * ) Notice: Subject to any disclaimer, the term of this patent is extended or adjusted under 35 U.S.C. 154(b) by 551 days.

(21) Appl. No.: 13/512,379

(22) PCT Filed: Aug. 26, 2010

(86) PCT No.: PCT/JP2010/064445
§ 371 (c)(1),
(2), (4) Date: May 29, 2012

(87) PCT Pub. No.: WO2011/065078
PCT Pub. Date: Jun. 3, 2011

(65) Prior Publication Data
US 2012/0237396 A1      Sep. 20, 2012

(30) Foreign Application Priority Data
Nov. 30, 2009   (JP) .................... 2009-272342

(51) Int. Cl.
| C09D 183/04 | (2006.01) |
| C09D 7/12 | (2006.01) |
| C09D 5/16 | (2006.01) |
| B01J 35/02 | (2006.01) |
| B01J 37/02 | (2006.01) |
| B01J 35/00 | (2006.01) |
| B01J 21/06 | (2006.01) |
| B01J 23/72 | (2006.01) |
| B01J 23/888 | (2006.01) |
| B01J 37/03 | (2006.01) |
| A61L 9/20 | (2006.01) |
| A61L 2/00 | (2006.01) |
| C08K 3/22 | (2006.01) |
| C08K 5/5415 | (2006.01) |
| C08K 5/5419 | (2006.01) |
| C08K 9/02 | (2006.01) |

(52) U.S. Cl.
CPC .............. *B01J 35/004* (2013.01); *B01J 21/063* (2013.01); *B01J 23/72* (2013.01); *B01J 23/888* (2013.01); *B01J 37/038* (2013.01); *C09D 5/1618* (2013.01); *C09D 7/1225* (2013.01); *C09D 183/04* (2013.01); *A61L 2/0076* (2013.01); *A61L 9/205* (2013.01); *C08K 3/22* (2013.01); *C08K 5/5415* (2013.01); *C08K 5/5419* (2013.01); *C08K 9/02* (2013.01)

(58) Field of Classification Search
CPC ....... C07B 37/06; B01J 23/888; B01J 35/004; A61L 9/20; A61L 2/00076
See application file for complete search history.

(56) References Cited

U.S. PATENT DOCUMENTS

| 2005/0126428 A1 | 6/2005 | Lee et al. |
| 2008/0081758 A1 | 4/2008 | Kuroda et al. |
| 2011/0005916 A1* | 1/2011 | Hashimoto et al. ...... 204/157.15 |

FOREIGN PATENT DOCUMENTS

| JP | 8-67835 | 3/1996 |
| JP | 08067835 A * | 3/1996 |
| JP | 11-12539 | 1/1999 |
| JP | 2000-95977 | 4/2000 |
| JP | 2004-154779 A | 6/2004 |
| JP | 3601532 | 10/2004 |
| JP | 2006-232729 A | 9/2006 |
| WO | 2009/116627 | 9/2009 |
| WO | 2010/050548 | 5/2010 |

OTHER PUBLICATIONS

Takeo Arai et al., "The enhancement of WO3-catalyzed photodegeneration of organic substances utilizing the redox cycle of copper ions", Journal of Applied Catalysis B. Environmental, vol. 84, No. 1-2, 2008, pp. 42-47.
Search report from International Application No. PCT/JP2010/064445, mail date is Nov. 22, 2010.
Extended European Search Report issued with respect to European Application No. 10832951.1, dated Jun. 13, 2013.

* cited by examiner

*Primary Examiner* — Anthony J Zimmer
*Assistant Examiner* — Syed Iqbal
(74) *Attorney, Agent, or Firm* — Greenblum & Bernstein, P.L.C.

(57) ABSTRACT

Object of the present invention is to provide visible light-responsive photocatalyst coating material which can form a coating film exhibiting superior allergen inactivation property through irradiation of visible light. The visible light-responsive photocatalyst coating material comprises: photocatalyst material having visible light-activity composed of metal oxide particle with divalent copper salt supported on the surface thereof, said metal oxide particle having optical semiconductor-characteristics and potential of valence band of said metal oxide particle being 3[V] or more (vs. SHE, pH=0); binder component including component having siloxane bond or component forming siloxane bond through reaction; and chloride ionic compound. When visible light is irradiated to the coating film, the metal oxide particle exhibits photocatalyst activity in the presence of the copper-divalent ion and chloride ion, thereby significantly high allergen inactivation property is exhibited. Additionally, it can prevent the separation of the photocatalyst coating material from the coating film.

11 Claims, No Drawings

VISIBLE LIGHT-RESPONSIVE PHOTOCATALYST COATING MATERIAL, COATED ARTICLE, ALLERGEN INACTIVATION METHOD

TECHNICAL FIELD

The present invention relates to: coating material including photocatalyst material having visible light activity; coated article formed using the coating material; and allergen inactivation method by irradiating visible light to the coated article to inactivate the allergen on the surface thereof.

BACKGROUND ART

Recent years, it has been recognized as a problem that asthma or allergy caused by allergens contained in tick excrement, carcass thereof, cedar pollen, and so on. Allergen is defined as a protein which reacts specifically with antibody of human (meaning of the protein includes glycoprotein). Along with recognition of such a problem, it has been increasingly interested in the influence of living environment on human health. Thus, the way to manage a household allergen has been recognized as a major issue for interior manufacturers or building product manufacturers.

It has been expected to use a photocatalyst material for handling materials including the household allergens. The photocatalyst material expresses oxidatively decomposing activity about some inorganic substance such as nitrogen oxide and organic substance, by utilizing light as energy source. Note that, light is low in its generating cost, and affects little load on the environment. Recently, thus, many studies have been carried out to apply photocatalyst materials to environmental cleaning, odor elimination, dirt elimination, sterilization, and so on. The photocatalyst material is also expected to degeneratively decompose the allergen.

Titanium oxide has been widely known as photocatalyst which exhibits activity under irradiation of UV-ray. However, photocatalyst material has need to exhibit the activity under irradiation of visible light in order to perform its function in interior of building, and therefore, such a photocatalyst material has been studied and developed.

For example, patent document 1 discloses a photocatalyst material exhibiting visible-light activity, which is composed of titanium oxide crystal in which oxygen atom sites are partially displaced by nitrogen atoms.

In the photocatalyst material disclosed in patent document 1, a part of oxygen atom sites of titanium oxide crystal are displaced by nitrogen atoms to make a new isolated level in the bandgap of titanium oxide, thereby the photocatalyst material is to exhibit the visible-light activity. When being exposed by a photon having energy larger than the bandgap energy between the isolated level and conduction band of titanium oxide, an electron in the isolated level is excited to the conduction band and a hole is generated in the isolated level, thereby the photocatalyst material exhibits the activity. Patent document 1: Japanese patent publication No. 3601532

SUMMARY OF INVENTION

Problems to be Resolved by the Invention

However, the abovementioned isolated level made in the bandgap of titanium oxide has a small potential, therefore the hole generated by the excitation of electron by visible light-exposure shows poor oxidizing power. Besides, the hole generated in the isolated level is restricted from freely migrating, therefore exhibiting a poor reactivity with target substrates for oxidization. As a result, the photocatalyst material disclosed in the patent document 1 exhibits a poor oxidative decomposition activity, albeit it has visible-light activity.

Therefore, the photocatalyst material of the patent document 1 achieves merely insufficient result for the inactivation of household allergen.

The present invention has been accomplished in view of the above problems, and has an object to provide: visible light-responsive photocatalyst coating material which exhibits high allergen inactivation property by irradiation of visible light; coated article utilizing such a high allergen inactivation property exhibited by the photocatalyst coating material; and allergen inactivation method utilizing the coated article.

Means of Solving the Problems

Visible light-responsive photocatalyst coating material of the present invention is characterized in comprising the following components of: photocatalyst material having visible light-activity composed of metal oxide particle with divalent copper salt supported on the surface of the metal oxide particle, said metal oxide particle having optical semiconductor-characteristics and potential of valence band of said metal oxide particle being 3[V] or more (vs. SHE, pH=0); binder component including component having siloxane bond or component forming siloxane bond through reaction; and chloride ionic compound.

Meaning of the visible light-activity is the characteristics of optical semiconductor that electron in valence band is excited through irradiation of light having wavelength of 400 [nm] or more, which being included in visible light range.

Therefore, when visible light is irradiated to a coating film formed of the visible light-responsive photocatalyst coating material, the metal oxide particle exhibits photocatalyst activity in the presence of the copper-divalent ion and chloride ion, thereby significantly high allergen inactivation property is exhibited. Furthermore, because siloxane bond derived from the binder component in the coating film has high bond energy, it can suppress the decomposition of the binder component arising from the photocatalyst. Therefore, it can prevent the separation of the photocatalyst material from the coating film.

In the present invention, it is preferred that said metal oxide particle includes particle of at least one sort selected from titanium dioxide, tungsten trioxide, and metal ion-doped titanium dioxide.

In this case, the coating film exhibits particularly-high allergen inactivation property.

In the present invention, it is preferred that said binder component includes at least one selected from tetra-alkoxysilane expressed in a general formula of $Si(OR)_4$ ("R" express identical or heterologous hydrocarbon group or phenyl group, the carbon number of which are 1~8), and partially hydrolyzed condensation polymer thereof.

In this case, because the above-described binder component has high hydrophilic property, it facilitates the adsorption of allergen having high affinity for water to the coating film, thereby the allergen inactivation property is further facilitated.

In the present invention, it is also preferred that said chloride ionic compound includes hydrochloric acid.

In this case, because the hydrochloric acid acts as a catalyst of hydrolysis reaction with the binder component, it facilitates the curing of the binder component. Therefore, it can improve the hardness and durability of the coating film.

Coated article of the present invention is characterized in that coating treatment of said visible light-responsive photocatalyst coating material is performed thereto.

By irradiating visible light which includes the wavelength excitable the visible light-responsible photocatalyst to the coated article, allergen on the surface of the coated article can be inactivated.

Allergen inactivation method of the present invention is characterized in comprising: irradiating visible light, which includes the wavelength excitable the visible light-responsible photocatalyst, onto the coating-treated surface of said coated article, thereby inactivating allergen on said surface.

By using this method, the allergen on the surface of the coated article can be inactivated.

Effect of the Invention

According to the present invention, the coating film formed of the visible light-responsive photocatalyst coating material exhibits high allergen inactivation property, and such an allergen inactivation property can be maintained for long periods.

Besides, the surface of the coated article, which the coating treatment of the visible light-responsive photocatalyst coating material is performed to, exhibits high allergen inactivation property, and such an allergen inactivation property can be maintained for long periods.

Besides, by using this coated article, allergen on the surface of the coated article can be significantly inactivated by the surface thereof.

BEST-MODE FOR CARRYING OUT THE INVENTION

Best mode for carrying out the present invention will be described below.

Visible light-responsive photocatalyst coating material includes: photocatalyst material; binder component; and chloride ionic compound.

The photocatalyst material is composed of metal oxide particle whose potential of valence band being 3[V] or more (vs. SHE, pH=0) and having optical semiconductor-characteristics, with divalent copper salt supported on the surface thereof. The metal oxide particle whose potential of valence band being 3[V] or more (vs. SHE, pH=0) and having optical semiconductor-characteristics is characterized as a material that, in case the divalent copper salt is supported on its surface, electron in the valence band thereof can be excited to generate a conduction electron and a hole, when a light having larger energy than the energy gap between the valence band and the conduction band of the crystal or a light having larger energy than the energy gap between the valence band and the oxidation-reduction potential of copper-univalent ion/copper-divalent ion is irradiated. The metal oxide particle is not particularly limited, so long as a valence band electron thereof can be excited by a light having wavelength of 400 [nm] or longer (which is included in a visible light-range). In short, abovementioned photocatalyst material is formed by making supported divalent copper salt on the surface of metal oxide particle whose potential of valence band being 3[V] or more (vs. SHE, pH=0) and having optical semiconductor-characteristics. The photocatalyst material has visible light-activity. The abovementioned metal oxide particle is a material, a valence band electron thereof can be excited by even a light having wavelength equal to or longer than 400 [nm]. Specific example of the metal oxide particle can include rutile-type titanium dioxide (potential of valence band thereof is 3[V] (vs. SHE, pH=0)), anatase-type titanium dioxide (potential of valence band thereof is 3[V] (vs. SHE, pH=0)), tungsten trioxide (potential of valence band thereof is 3.1~3.2[V] (vs. SHE, pH=0)), titanium dioxide with which metal ion (such as cerium) being doped (potential of valence band of cerium-doped titanium dioxide is 3[V] (vs. SHE, pH=0)), and so on. Metal ion for being doped with the titanium dioxide can include such as germanium, vanadium, gallium, tungsten, in addition to the cerium.

The metal oxide particle is preferably in a shape of fine particle. Although particle size of the metal oxide particle is not particularly limited, it is preferable to be 1 [µm] or less, and further preferable to be 500 [nm] or less. The smaller the particle size is, the surface area of the metal oxide particle increases. The photocatalyst activity is exerted at the surface of the metal oxide particle, therefore allergen inactivation property thereof increases with reduction of the particle size. Although lower limit of the particle size is not particularly limited, it is generally in the order of 5 [nm].

As to the amount of the divalent copper salt supported on the metal oxide particle, it is preferred that ratio of copper content in the divalent copper salt with respect to the metal oxide particle is desirably set in a range of 0.0001 to 1 percent by weight. In the photocatalyst material, the metal oxide particle is excited by light. Therefore, if the considerable area of the surface of the metal oxide particle is covered by the divalent copper salt, it disturbs the light irradiation on the metal oxide particle, and photocatalyst activity may be decreased. Furthermore, divalent copper salt acts as a multi-electron reduction catalyst of oxygen. Therefore, it is desirable that the divalent copper salt is supported on the metal oxide particle in a form of highly dispersive microscopic particles, not agglomerated, so as to effectively exhibit the catalyst activity. Thus, as to the amount of supported the divalent copper salt, ratio of copper content with respect to the metal oxide particle is preferably 1 percent or less by weight. On the other hand, if the amount of supported divalent copper salt is too little, function of the divalent copper salt as the multi-electron reduction catalyst may be insufficient. Thus, ratio of copper content with respect to the metal oxide particle is preferably 0.0001 percent or more by weight.

Anion of the divalent copper salt is preferably hydroxide ion. For example, copper chloride ($CuCl_2.2H_2O$) can be used for the starting material of the divalent copper salt. copper nitrate ($Cu(NO_3)_2.3H_2O$) also can be used for the starting material of the divalent copper salt.

Aqueous solution impregnation process can be used for a method of making the divalent copper salt supported on the surface of metal oxide particle, but it is not particularly limited. By using this process, the divalent copper salt is supported on the surface of metal oxide particle as highly dispersive microscopic particle, and the anion of the divalent copper salt is hydroxide ion. In this process, Cu(II) is estimated to be in a state of 6-coordination. The divalent copper salt is, specifically, estimated to be in a state of M-O—$Cu(OH)_3.3H_2O$ if it is bound with oxygen atom of the metal oxide particle, and to be in a state of $Cu(OH)_2.4H_2O$ if it is adsorbed.

The binder component cures during the processes of drying, heating, and the like of the visible light-responsive photocatalyst coating material, thereby the binder component holds the photocatalyst material so as not to separate from the photocatalyst coating material. Thereby, it can persist the inactivation property to the allergen. The binder component includes a component having siloxane bond or forming siloxane bond through reaction. Especially, the binder component may include a component having siloxane bond or forming siloxane bond through reaction with water. Such as silicon acrylic resin, silicone composition, partially hydrolyzed condensation polymer of these, and the like may be recited as the component having siloxane bond. Because siloxane bond is not degraded by the photocatalyst, it can ensure the durability of coating film formed of the visible light-responsive photocatalyst coating material.

Especially, the component having siloxane bond or forming siloxane bond through reaction is preferably a tetraalkoxysilane expressed in a general formula of $Si(OR)_4$ (herein, "R" express identical or heterologous hydrocarbon group or phenyl group, the carbon number of which are 1~8) or partially hydrolyzed condensation polymer thereof. In this case, it facilitates the adsorption of an allergenic protein having high affinity for water to the coating film formed of the visible light-responsive photocatalyst coating material. As a result, it can facilitate the allergen inactivation property of the coating film.

The silicone composition expressed in a general formula of $Si(OR)_4$ is not particularly limited except that four radicals "R" are independent, respectively, and each of radicals "R" is composed of hydrocarbon group or phenyl group the carbon number of which is 1~8. It is prefer that this silicone composition is, particularly, tetramethoxysilane, tetraethoxysilane, tetra-n-propoxysilane, tetraisopropoxysilane, tetra-n-butoxysilane, tetraisobutoxysilane, tetra-sec-butoxysilane, or tetra-t-butoxysilane.

As discussed later, the chloride ionic compound contributes to the improvement of the allergen inactivation property by the exhibition of photocatalyst activation of the photocatalyst material. The chloride ionic compound is preferably hydrogen chloride, but it is not particularly limited. Hydrogen chloride behaves as a catalyst for hydrolysis reaction of a component having siloxane bond. Therefore, hydrogen chloride facilitates the curing of the binder component, and can improve the hardness and/or durability of the coating film. Apart from such a configuration, it can use an acid or a base other than chloride ionic compound as a catalyst for the hydrolysis reaction, and a chloride ionic compound such as potassium chloride may be contained in the visible light-responsive photocatalyst coating material aside from the catalyst.

A coating film which exerts remarkably high allergen inactivation property can be formed, by curing the visible light-responsive photocatalyst coating material containing above-mentioned components to form a film. Because potential of valence band of the metal oxide particles, composed of the photocatalyst material of the coating film, is 3[V] or more (vs. SHE, pH=0), the oxidizability of a hole generated by the irradiation of light to the photocatalyst material is high enough to denature/degrade to inactivate the allergen. Moreover, because the metal oxide particle has visible light-activity, the allergen inactivation property can be exerted even in an indoor environment in which inactivation of the allergen is especially needed, under the visible light-irradiation by such as a fluorescent lamp.

Furthermore, a new knowledge has found that exceedingly-high allergen inactivation property can be exerted when the photocatalyst activation of the photocatalyst material is activated under presence of copper-divalent ion and chlorine ion. In other words, it has found that, when the oxidation effect due to the exertion of the photocatalyst activation by the photocatalyst material is activated under the condition where copper-divalent ion and chlorine ion are coordinated with allergen, the allergenicity of the allergen is lost in a remarkably rapid manner. The present visible light-responsive photocatalyst coating material utilizes this new knowledge.

The contained amounts of the photocatalyst material, the binder component, and the chloride ionic compound in the visible light-responsive photocatalyst coating material are properly determined according to the aspects of usage of the visible light-responsive photocatalyst coating material, in consideration of the film forming property of the coating film, enough exertion of the allergen inactivation property, and so on.

It is preferred that the contained amount of the photocatalyst material with respect to the total mass of solid content of the visible light-responsive photocatalyst coating material is within the range of 30 to 90 percent by mass. If this contained amount is less than 30 percent by mass, the allergen inactivation property of the photocatalyst material might be insufficient. If this contained amount is more than 90 percent by mass, hardness and/or durability of the coating film formed of the visible light-responsive photocatalyst coating material might be insufficient.

It is preferred that the contained amount of the binder component with respect to the total mass of solid content of the visible light-responsive photocatalyst coating material is within the range of 10 to 70 percent by mass. If this contained amount is less than 10 percent by mass, hardness and/or durability of the coating film formed of the visible light-responsive photocatalyst coating material might be insufficient. If this contained amount is more than 70 percent by mass, the allergen inactivation property of the photocatalyst material might be insufficient due to that the surface of the photocatalyst material is covered over by the binder component in the coating film. Particularly, it is preferred that the contained amount of the component having siloxane bond or forming siloxane bond through reaction in the binder component with respect to the total mass of solid content of the binder component is within the range of 10 to 100 percent by mass. If this contained amount is less than 10 percent by mass, the durability of the coating film might be decreased due to that the binder component is degraded by oxidative decomposition property of the photocatalyst inside the coating film formed of the visible light-responsive photocatalyst coating material.

It is preferred that the contained amount of the chloride ionic compound with respect to the total mass of solid content of the visible light-responsive photocatalyst coating material is within the range of 0.001 to 0.01 percent by mass. If this contained amount is less than 0.001 percent by mass, the allergen inactivation property might be insufficient. If this contained amount is more than 0.01 percent by mass, hardness and/or durability of the coating film formed of the visible light-responsive photocatalyst coating material might be insufficient.

As necessary, the visible light-responsive photocatalyst coating material is preferred to contain proper solvent so as to ensure better coating property. In particular, if water is used as the solvent, it can facilitate the curing reaction of the component having siloxane bond in the visible light-responsive photocatalyst coating material. Note that, if aqueous dispersion of photocatalyst material is used during the process of combining the photocatalyst material in the visible light-responsive photocatalyst coating material, this water in the aqueous dispersion can be used as all or part of the solvent of the visible light-responsive photocatalyst coating material.

A coated article can be obtained by performing coating treatment to the surface of a proper treat-target article with this visible light-responsive photocatalyst coating material. The coated article exerts good allergen inactivation property at its surface. The coated article is effective, especially, to inactivate the so-called inhalant allergen such as allergens contained in house dust, dandruff, pollen, fungus, insect, and so on.

The treat-target article is not particularly limited, and it may be, for example, furniture or bedclothes such as sofa or bed, building material such as floor material, fiber or fiber product such as wallpaper, soft toy, filter, carpet, curtain, and so on.

For the coating treatment to the treat-target article, the coating film is formed by: applying or impregnating the visible light-responsive photocatalyst coating material to the surface of the treat-target article, depending on the kinds of the treat-target article; and thereafter curing to form a film by appropriate method such as heating, depending on the composition of the binder component and presence or absence of the solvent.

Allergen can be inactivated by using the abovementioned coated article and irradiating the coating-treated-surface of the coated article with visible light which includes the wavelength excitable the visible light-responsive photocatalyst.

Specific method for inactivating allergens by using the coated article may include such a method in which arranging the coated article in an allergen existing space and irradiating the coated article with visible light. The visible light irradiating method may include irradiation of sunlight to the coated article, irradiation of visible light from a light apparatus which emits visible light to the coated article, and so on.

In case that the coated article is a filter, it can use an air cleaner provided with: the abovementioned coated article; a lighting device configured to irradiate the coated article with visible light; and a blower including such as a fan for blowing air draft to the coated article. In this case, when arranging the air cleaner in an allergen existing space and turning on the blower and the lighting device, the air in the space is blown to the coated article and allergen in the air can be inactivated.

Particularly, in case that the coated article is floor material, allergen in a space in which the floor material is arranged can be inactivated, by irradiating visible light to the coating film of this floor material if a material containing the allergen and floating in the space falls onto the floor material.

This floor material is preferred to have asperity at the coating treated surface. Especially, it is preferred, the floor material has such an asperity that when a 10 [cm] diameter spherical body is put on the surface of this floor material, there remains a region of the floor material which does not contact with the abovementioned spherical body. Furthermore, the projected area in a planar view of such the region is preferably 10 percent or more with respect to the total projected area in a planar view of the surface of the floor material. It is generally supposed that: allergen containing material is usually lays on a floor surface; the allergen containing material is disturbed to be scattered in the air by such as walking of a human; a human absorbs the material with the breathing; and thereby the human experiences symptoms of such as allergic rhinitis or asthma. In the case where the abovementioned asperities are formed at the surface of the floor material, there is formed a large number of regions which are not likely to contact with sole of the human during walking at the surface of the floor material. Therefore, the allergen containing material deposited on these regions is not likely to disturbed by walking of a human. As a result, allergen can be effectively inactivated by the coating film at the surface of the floor material, through irradiation of visible light to the surface of the coating film.

The method for preparing the asperity is not particularly limited. For example, the method may include: treating a concavo-convex-press to the floor material to transfer the concavo-convex shape to the surface of the floor material; cutting the surface of the floor material to form the asperity; forming, at least the surface part of, the floor material by fiber bundle and so on; forming recessed areas by preparing the floor materials in brick-shape or tile-shape; and so on.

EXAMPLES

Specific examples of the present invention are described below. Note that, the present invention is not limited in the following examples.

Example 1

$WO_3$ powder (average grain size is 250 [nm], manufactured by Kojundo Chemical Laboratory Co., Ltd.) was prepared, and the powder was passed through a filter to filter out the particles having the grain size of 1 [µm] or more. After then, the filtered powder was burned at 650 [° C.] for 3 hours, as a prior processing. Thereby, tungsten trioxide fine particles were obtained.

The tungsten trioxide fine particles were added in distilled water so that the ratio of the tungsten trioxide fine particles to distilled water was 10 percent by mass, and suspended. $Cu(NO_3)_2 \cdot 3H_2O$ (manufactured by Wako Pure Chemical Industries, Ltd.) was added in the suspension liquid so that the ratio of copper ion to the tungsten trioxide fine particles were 0.1 percent by mass, and the mixture was heated with agitation to 90 [° C.] for 1 hour. Next, this suspending liquid was filtered by suction filtration. After then, the residue was washed with distilled water, and the residue after wash was heat dried at 110 [° C.]. Thereby, tungsten trioxide with supported divalent copper salt fine particles were obtained.

The tungsten trioxide with supported divalent copper salt fine particles were, powderized by use of mortar, added in distilled water so that the ratio of the powder to the distilled water was 10 percent by mass, suspended by ultrasonic dispersion, and stationary kept for 24 hours. Then, obtaining the supernatant liquid from the stationary kept liquid, thereby "dispersion liquid of tungsten trioxide with supported divalent copper salt fine particles" was obtained. The contained amount of the tungsten trioxide with supported divalent copper salt fine particles in the dispersion liquid was verified to be 3.6 percent by mass, by way of heat drying a part of this dispersion liquid.

Next, 5 parts by mass of tetraethoxysilane (manufactured by Wako Pure Chemical Industries, Ltd.), 0.8 parts by mass of ion-exchanged water, 0.07 parts by mass of hydrochloric acid of 0.1 [mol/l] concentration, and 94.13 parts by mass of ethanol, were mixed in a reaction container, and agitated for 16 hours, thereby solution of partially hydrolyzed condensation polymer of tetraethoxysilane was obtained.

100 parts by mass of the solution of the partially hydrolyzed condensation polymer of tetraethoxysilane was mixed with 100 parts by mass of the abovementioned dispersion liquid of tungsten trioxide with supported divalent copper salt fine particles, and agitated it for 1 hour, thereby visible light-responsive photocatalyst coating material was obtained.

The visible light-responsive photocatalyst coating material was applied on a 50 [mm] square clean glass plate by spin coating, dried the applied coat to be cured by heating for 30 minutes at 100 [° C.], thereby visible light-responsive photocatalyst coated article was obtained as an evaluation sample.

Example 2

Rutile-type titanium dioxide (MT-150A manufactured by Tayca Corporation) was added in distilled water so that the ratio of the rutile-type titanium dioxide to distilled water was 10 percent by mass, and suspended. $Cu(NO_3)_2 \cdot 3H_2O$ (manufactured by Wako Pure Chemical Industries, Ltd.) was added in the suspension liquid so that the ratio of copper ion to the rutile-type titanium dioxide was 0.1 percent by mass, and the mixture was heated with agitation to 90 [° C.] for 1 hour. Next, this suspending liquid was filtered by suction filtration. After then, the residue was washed with distilled water, and then the residue after wash was heat dried at 110 [° C.]. Thereby, rutile-type titanium dioxide with supported divalent copper salt fine particles were obtained.

The rutile-type titanium dioxide with supported divalent copper salt fine particles were, powderized by use of mortar, added in distilled water so that the ratio of the rutile-type titanium dioxide with supported divalent copper salt fine particles to the distilled water was 10 percent by mass, suspended by ultrasonic dispersion, and stationary kept for 24 hours. Then, obtaining the supernatant liquid from the stationary kept liquid, thereby "dispersion liquid of rutile-type titanium dioxide with supported divalent copper salt fine particles" was obtained. The contained amount of the rutile-type titanium dioxide with supported divalent copper salt fine particles in the dispersion liquid was verified to be 6.1 percent by mass, by way of heat drying a part of this dispersion liquid.

Next, 5 parts by mass of tetraethoxysilane (manufactured by Wako Pure Chemical Industries, Ltd.), 0.8 parts by mass of ion-exchanged water, 0.07 parts by mass of hydrochloric acid of 0.1 [mol/l] concentration, and 94.13 parts by mass of ethanol, were mixed in a reaction container, and agitated for 16 hours, thereby solution of partially hydrolyzed condensation polymer of tetraethoxysilane was obtained.

100 parts by mass of the solution of the partially hydrolyzed condensation polymer of tetraethoxysilane was mixed with 100 parts by mass of the abovementioned dispersion liquid of rutile-type titanium dioxide with supported divalent copper salt fine particles, and agitated it for 1 hour, thereby visible light-responsive photocatalyst coating material was obtained.

The visible light-responsive photocatalyst coating material was applied on a 50 [mm] square clean glass plate by spin coating, dried the applied coat to be cured by heating for 30 minutes at 100 [° C.], thereby visible light-responsive photocatalyst coated article was obtained as an evaluation sample.

Example 3

In the process of the Example 1, 0.07 parts by mass of nitric acid of 0.1 [mol/l] concentration was used as substitute for the 0.07 parts by mass of hydrochloric acid of 0.1 [mol/l] concentration during the obtaining process of the partially hydrolyzed condensation polymer of tetraethoxysilane, and 0.0005 parts by mass of potassium chloride was added during the obtaining process of the visible light-responsive photocatalyst coating material. Other conditions were set to be same with the processes of the Example 1. Thereby, visible light-responsive photocatalyst coating material and visible light-responsive photocatalyst coated article as an evaluation sample were obtained.

Example 4

The dispersion liquid of tungsten trioxide with supported divalent copper salt fine particles were obtained in a same process with the Example 1.

Next, 5 parts by mass of methyltrimethoxysilane (manufactured by Wako Pure Chemical Industries, Ltd.), 1 parts by mass of ion-exchanged water, 0.07 parts by mass of hydrochloric acid of 0.1 [mol/l] concentration, and 93.93 parts by mass of ethanol, were mixed in a reaction container, and agitated for 16 hours, thereby solution of partially hydrolyzed condensation polymer of methyltrimethoxysilane was obtained.

100 parts by mass of the solution of the partially hydrolyzed condensation polymer of methyltrimethoxysilane was mixed with 100 parts by mass of the abovementioned dispersion liquid of tungsten trioxide with supported divalent copper salt fine particles, and agitated it for 1 hour, thereby visible light-responsive photocatalyst coating material was obtained.

The visible light-responsive photocatalyst coating material was applied on a 50 [mm] square clean glass plate by spin coating, dried the applied coat to be cured by heating for 30 minutes at 100 [° C.], thereby visible light-responsive photocatalyst coated article was obtained as an evaluation sample.

Comparative Example 1

Anatase-type titanium dioxide (ST-01 manufactured by ISHIHARA SANGYO KAISHA, LTD.) was annealed for 3 hours under 550 [° C.] in the ammonia air draft (1 SCCM). Thereby, nitrogen-doped titanium dioxide fine particles having isolated level of less than 3[V] (vs. SHE, pH=0) were obtained.

The nitrogen-doped titanium dioxide fine particles were added in distilled water so that the ratio of the nitrogen-doped titanium dioxide fine particles to distilled water was 10 percent by mass, suspended by ultrasonic dispersion, and stationary kept for 24 hours. Then, obtaining the supernatant liquid from the stationary kept liquid, thereby "dispersion liquid of nitrogen-doped titanium dioxide fine particles" was obtained. The contained amount of the nitrogen-doped titanium dioxide fine particles in the dispersion liquid was verified to be 2.5 percent by mass, by way of heat drying a part of this dispersion liquid.

Next, 5 parts by mass of tetraethoxysilane (manufactured by Wako Pure Chemical Industries, Ltd.), 0.8 parts by mass of ion-exchanged water, 0.07 parts by mass of hydrochloric acid of 0.1 [mol/l] concentration, and 94.13 parts by mass of ethanol, were mixed in a reaction container, and agitated for 16 hours, thereby solution of partially hydrolyzed condensation polymer of tetraethoxysilane was obtained.

100 parts by mass of the solution of the partially hydrolyzed condensation polymer of tetraethoxysilane was mixed with 150 parts by mass of the abovementioned dispersion liquid of nitrogen-doped titanium dioxide fine particles, and agitated it for 1 hour, thereby visible light-responsive photocatalyst coating material was obtained.

The visible light-responsive photocatalyst coating material was applied on a 50 [mm] square clean glass plate by spin coating, dried the applied coat to be cured by heating for 30 minutes at 100 [° C.], thereby visible light-responsive photocatalyst coated article was obtained as an evaluation sample.

Comparative Example 2

Nitrogen-doped titanium dioxide fine particles obtained by the same process with the comparative example 1 were added in distilled water so that the ratio of the nitrogen-doped titanium dioxide fine particles to distilled water was 10 percent by mass, and suspended. $Cu(NO_3)_2 \cdot 3H_2O$ (manufactured by Wako Pure Chemical Industries, Ltd.) was added in the suspension liquid so that the ratio of copper ion to the nitrogen-doped titanium dioxide fine particles was 0.1 percent by mass, and the mixture was heated with agitation to 90 [° C.] for 1 hour. Next, this suspending liquid was filtered by suction filtration. After then, the residue was washed with distilled water, and then the residue after wash was heat dried at 110 [°

C.]. Thereby, nitrogen-doped titanium dioxide with supported divalent copper salt fine particles were obtained.

The nitrogen-doped titanium dioxide fine particles were, powderized by use of mortar, added in distilled water so that the ratio of the nitrogen-doped titanium dioxide to the distilled water was 10 percent by mass, suspended by ultrasonic dispersion, and stationary kept for 24 hours. Then, obtaining the supernatant liquid from the stationary kept liquid, thereby "dispersion liquid of nitrogen-doped titanium dioxide with supported divalent copper salt fine particles" was obtained. The contained amount of the nitrogen-doped titanium dioxide with supported divalent copper salt fine particles in the dispersion liquid was verified to be 2.5 percent by mass, by way of heat drying a part of this dispersion liquid.

Next, 5 parts by mass of tetraethoxysilane (manufactured by Wako Pure Chemical Industries, Ltd.), 0.8 parts by mass of ion-exchanged water, 0.07 parts by mass of hydrochloric acid of 0.1 [mol/l] concentration, and 94.13 parts by mass of ethanol, were mixed in a reaction container, and agitated for 16 hours, thereby solution of partially hydrolyzed condensation polymer of tetraethoxysilane was obtained.

100 parts by mass of the solution of the partially hydrolyzed condensation polymer of tetraethoxysilane was mixed with 100 parts by mass of the abovementioned dispersion liquid of nitrogen-doped titanium dioxide with supported divalent copper salt fine particles, and agitated it for 1 hour, thereby visible light-responsive photocatalyst coating material was obtained.

The visible light-responsive photocatalyst coating material was applied on a 50 [mm] square clean glass plate by spin coating, dried the applied coat to be cured by heating for 30 minutes at 100 [° C.], thereby visible light-responsive photocatalyst coated article was obtained as an evaluation sample.

Comparative Example 3

5 parts by mass of tetraethoxysilane (manufactured by Wako Pure Chemical Industries, Ltd.), 0.8 parts by mass of ion-exchanged water, 0.07 parts by mass of hydrochloric acid of 0.1 [mol/l] concentration, and 94.13 parts by mass of ethanol, were mixed in a reaction container, and agitated for 16 hours, thereby solution of partially hydrolyzed condensation polymer of tetraethoxysilane was obtained.

100 parts by mass of the solution of the partially hydrolyzed condensation polymer of tetraethoxysilane, 10 parts by mass of dispersion liquid of anatase-type titanium dioxide (STS-01 manufactured by ISHIHARA SANGYO KAISHA, LTD.; contained amounts of titanium dioxide therein is 30 percent by mass), and 0.001 parts by mass of copper chloride dihydrate were mixed, and agitated it for 1 hour, thereby ultraviolet light-responsive photocatalyst coating material was obtained.

The ultraviolet light-responsive photocatalyst coating material was applied on a 50 [mm] square clean glass plate by spin coating, dried the applied coat to be cured by heating for 30 minutes at 100 [° C.], thereby ultraviolet light-responsive photocatalyst coated article was obtained as an evaluation sample.

Comparative Example 4

WO$_3$ powder (average grain size is 250 [nm], manufactured by Kojundo Chemical Laboratory Co., Ltd.) was prepared, and the powder was passed through a filter to filter out the particles having the grain size of 1 [μm] or more. After then, the filtered powder was burned at 650 [° C.] for 3 hours, as a prior processing. Thereby, tungsten trioxide fine particles were obtained.

The tungsten trioxide fine particles were added in distilled water so that the ratio of the tungsten trioxide fine particles to distilled water was 10 percent by mass, suspended by ultrasonic dispersion, and stationary kept for 24 hours. Then, obtaining the supernatant liquid from the stationary kept liquid, thereby "dispersion liquid of tungsten trioxide fine particles" was obtained. The contained amount of the titanium trioxide fine particles in the dispersion liquid was verified to be 3.8 percent by mass, by way of heat drying a part of this dispersion liquid.

Next, 5 parts by mass of tetraethoxysilane (manufactured by Wako Pure Chemical Industries, Ltd.), 0.8 parts by mass of ion-exchanged water, 0.07 parts by mass of hydrochloric acid of 0.1 [mol/l] concentration, and 94.13 parts by mass of ethanol, were mixed in a reaction container, and agitated for 16 hours, thereby solution of partially hydrolyzed condensation polymer of tetraethoxysilane was obtained.

100 parts by mass of the solution of the partially hydrolyzed condensation polymer of tetraethoxysilane was mixed with 100 parts by mass of the abovementioned dispersion liquid of tungsten trioxide fine particles, and agitated it for 1 hour, thereby visible light-responsive photocatalyst coating material was obtained.

The visible light-responsive photocatalyst coating material was applied on a 50 [mm] square clean glass plate by spin coating, dried the applied coat to be cured by heating for 30 minutes at 100 [° C.], thereby visible light-responsive photocatalyst coated article was obtained as an evaluation sample.

Comparative Example 5

In the process of the Example 1, 0.07 parts by mass of nitric acid of 0.1 [mol/l] concentrations was used as substitute for the 0.07 parts by mass of hydrochloric acid of 0.1 [mol/l] concentrations during the obtaining process of the partially hydrolyzed condensation polymer of tetraethoxysilane. Other conditions were set to be same with the process of the Example 1. Thereby, visible light-responsive photocatalyst coating material and visible light-responsive photocatalyst coated article as an evaluation sample were obtained.

Comparative Example 6

The dispersion liquid of tungsten trioxide with supported divalent copper salt fine particles was obtained in a same process with the Example 1.

100 parts by mass of the dispersion liquid of tungsten trioxide with supported divalent copper salt fine particles, 2 parts by mass of acrylic emulsion lacquer (VONCOAT VF-1060; manufactured by DIC Corporation), and 0.0005 parts by mass of potassium chloride were mixed, and agitated it for 1 hour, thereby visible light-responsive photocatalyst coating material was obtained.

The visible light-responsive photocatalyst coating material was applied on a 50 [mm] square clean glass plate by spraying, dried the applied coat to be cured by heating for 30 minutes at 100 [° C.], thereby visible light-responsive photocatalyst coated article was obtained as an evaluation sample.

[Evaluation of the Performance]

The performances of the evaluation samples obtained in the above "examples" and "comparative examples" have been evaluated. Details of the evaluations are described below.

(Pre-Treatment)

As a pre-treatment, the evaluation sample was enclosed in a tedlar bag whose bag-size was 3 [L], with appropriate amount of pure-air. After then, ultraviolet light was irradiated to the sample by a black light (Handy UV Lamp LUV-16; manufactured by AS ONE Corporation) for 24 hours in a condition where the intention of ultraviolet radiation at the surface of the evaluation sample was 1 [mW/cm$^2$]. Such the sample for evaluation was used for the evaluation tests below.

(Test for Allergen Inactivation Property)

Allergen (purified mite antigen Derf 1; manufactured by ASAHI BREWERIES, LTD.) was added in buffer solution (obtained by diluting the buffer for biochemistry of "20X PBS Tween-20 Buffer" twentyfold by ultrapure water; "20X PBS Tween-20 Buffer" was manufactured by TAKARA BIO INC.) so that the concentration of the allergen was 33.3 [ng/L], thereby allergen solution was obtained. 0.4 [ml] of this allergen solution was dropped on the evaluation sample, and then, the evaluation sample was covered by a 40 [mm] square film.

After then, visible light is irradiated to the evaluation sample for 24 hours so that the illumination intensity at the surface of the sample is 2000 [lx]. Herein, the visible light is obtained by filtering the light of a white fluorescent lamp by use of an ultraviolet light-cut filter which cuts the wavelength below 400 [nm].

Then, the allergen solution was collected from the film. Concentration of the allergen in the allergen solution was determined by Enzyme-linked immunosorbent assay method (ELISA method). The concentration change of the allergen in the allergen solution was calculated on percentage, thereby the degree of the inactivation of the allergen was evaluated.

(Pencil Hardness Test)

The hardness of the surface of the coating film of the evaluation sample was measured by pencil method according to JISK5600-5-4.

(Accelerated Weathering Resistance Test)

The weathering resistance of the surface of the coating film of the evaluation sample was evaluated by the accelerated weathering method (Xenon lamp method) according to JISK5600-7-7. On the assumption that the coated article being used in a household, it was evaluated by the cycle C test in which the test plate was not wetted. After the continuous exposure for 50 hours, the outer appearance of the evaluation sample was observed in visual. The weathering resistance of the coating film was evaluated according to the following criteria.

○: there was no change in the outer appearance between before and after the weathering test.

x: there was visible change in the outer appearance between before and after the weathering test.

The results of evaluations are shown in Table 1.

TABLE 1

| | photocatalyst material | binder component | chloride ionic compound | concentration change of allergen | pencil hardness | weathering resistance |
|---|---|---|---|---|---|---|
| Example 1 | Cu(II)/WO$_3$ | condensation polymer of tetraethoxysilane | hydrochloric acid | 88% | H | ○ |
| Example 2 | Cu(II)/TiO$_2$(rutile) | condensation polymer of tetraethoxysilane | hydrochloric acid | 76% | F | ○ |
| Example 3 | Cu(II)/WO$_3$ | condensation polymer of tetraethoxysilane | potassium chloride | 90% | B | ○ |
| Example 4 | Cu(II)/WO$_3$ | condensation polymer of methyltrimethoxysilane | hydrochloric acid | 72% | H | ○ |
| Comparative example 1 | Nitrogen-doped TiO$_2$(anatase) | condensation polymer of tetraethoxysilane | hydrochloric acid | 14% | B | ○ |
| Comparative example 2 | Cu(II)/Nitrogen-doped TiO$_2$(anatase) | condensation polymer of tetraethoxysilane | hydrochloric acid | 17% | B | ○ |
| Comparative example 3 | TiO$_2$(anatase) | condensation polymer of tetraethoxysilane | copper chloride and hydrochloric acid | 8% | 2H | ○ |
| Comparative example 4 | WO$_3$ | condensation polymer of tetraethoxysilane | hydrochloric acid | 20% | H | ○ |
| Comparative example 5 | Cu(II)/WO$_3$ | condensation polymer of tetraethoxysilane | — | 47% | B | ○ |
| Comparative example 6 | Cu(II)/WO$_3$ | acrylic emulsion | potassium chloride | 83% | less than 2B | x |

As shown in Table 1, the examples 1 to 4 have superior performances compared with the comparative examples 1 to 6.

The invention claim is:

1. Visible light-responsive photocatalyst coating material comprising:
   photocatalyst material having visible light-activity composed of metal oxide particle with divalent copper salt supported on the surface of the metal oxide particle, said metal oxide particle having potential of valence band being 3[V] or more vs. SHE, pH=0;
   binder component including component having siloxane bond or capable of forming siloxane bond through reaction; and
   chloride ionic compound.

2. The visible light-responsive photocatalyst coating material as set forth in claim 1, wherein said metal oxide particle includes particle of at least one sort selected from titanium dioxide; tungsten trioxide; and metal ion-doped titanium dioxide.

3. The visible light-responsive photocatalyst coating material as set forth in claim 1, wherein said binder component includes at least one selected from tetra- alkoxysilane expressed in a general formula of Si(OR)$_4$ in which "R" express identical or heterologous hydrocarbon group or phenyl group, the carbon number of which are 1~8; and partially hydrolyzed condensation polymer thereof.

4. The visible light-responsive photocatalyst coating material as set forth in claim 2, wherein said binder component includes at least one selected from tetra-alkoxysilane expressed in a general formula of $Si(OR)_4$ in which "R" express identical or heterologous hydrocarbon group or phenyl group, the carbon number of which are 1~8; and partially hydrolyzed condensation polymer thereof.

5. The visible light-responsive photocatalyst coating material as set forth in claim 1, wherein said chloride ionic compound includes hydrochloric acid.

6. The visible light-responsive photocatalyst coating material as set forth in claim 2, wherein said chloride ionic compound includes hydrochloric acid.

7. The visible light-responsive photocatalyst coating material as set forth in claim 3, wherein said chloride ionic compound includes hydrochloric acid.

8. The visible light-responsive photocatalyst coating material as set forth in claim 4, wherein said chloride ionic compound includes hydrochloric acid.

9. A coated article, wherein coating treatment of said visible light-responsive photocatalyst coating material as set forth claim 1 is performed thereto.

10. An allergen inactivation method comprising:
irradiating visible light onto the coating-treated surface of the coated article as set forth in claim 9, said visible light including the wavelength which excites the visible light-responsive photocatalyst, thereby inactivating allergen on said surface.

11. The visible light-responsive photocatalyst coating material as set forth in claim 1, wherein said chloride ionic compound includes potassium chloride.

* * * * *